(12) United States Patent
Molland et al.

(10) Patent No.: US 10,188,534 B2
(45) Date of Patent: Jan. 29, 2019

(54) STENT HAVING REDUCED PASSAGE OF EMBOLI AND STENT DELIVERY SYSTEM

(75) Inventors: Doug Molland, Excelsior, MN (US); Jianlu Ma, Maple Grove, MN (US); Joe Tatalovich, St. Louis Park, MN (US); Jeff Vogel, Brooklyn Park, MN (US); Josh Dudney, Minneapolis, MN (US); Mark Vandlik, Shorewood, MN (US); Richard Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 1971 days.

(21) Appl. No.: 11/939,627

(22) Filed: Nov. 14, 2007

(65) Prior Publication Data

US 2008/0167708 A1 Jul. 10, 2008

Related U.S. Application Data

(60) Provisional application No. 60/866,311, filed on Nov. 17, 2006.

(51) Int. Cl.
*A61F 2/90* (2013.01)
*A61F 2/91* (2013.01)

(52) U.S. Cl.
CPC .......... *A61F 2/90* (2013.01); *A61F 2/91* (2013.01); *A61F 2210/0057* (2013.01); *A61F 2210/0076* (2013.01); *A61F 2220/0041* (2013.01); *A61F 2250/0023* (2013.01); *A61F 2250/0048* (2013.01)

(58) Field of Classification Search
CPC .... A61F 2/91; A61F 2/915; A61F 2002/9155; A61F 2002/91533; A61F 2002/91525; A61F 2002/91516; A61F 2002/91508; A61F 2250/0023; A61F 2250/0024

USPC ....... 606/151, 200; 623/1.39, 1.4, 1.46, 1.17
See application file for complete search history.

(56) References Cited

U.S. PATENT DOCUMENTS

| | | | | |
|---|---|---|---|---|
| 5,637,113 A | * | 6/1997 | Tartaglia et al. | 623/1.42 |
| 5,674,241 A | * | 10/1997 | Bley et al. | 623/1.2 |
| 5,788,626 A | * | 8/1998 | Thompson | 623/1.15 |
| 6,039,755 A | * | 3/2000 | Edwin et al. | 623/1.15 |
| 6,165,211 A | * | 12/2000 | Thompson | 623/1.13 |
| 6,358,274 B1 | | 3/2002 | Thompson | |

(Continued)

FOREIGN PATENT DOCUMENTS

WO 2002038080 A2 5/2002
WO WO-2002/038080 A2 5/2002

(Continued)

OTHER PUBLICATIONS

Examination Report from counterpart European Patent Application No. 07254489.3, dated Apr. 21, 2015, 4 pp.

(Continued)

*Primary Examiner* — David C Eastwood
(74) *Attorney, Agent, or Firm* — Shumaker & Sieffert, P.A.

(57) ABSTRACT

A stent for reducing the passage of emboli into body lumen once deployed includes a structural portion and a barrier portion. The structural portion, when expanded in a conduit, provides sufficient strength to maintain an open lumen in the conduit. The barrier portion reduces migration of emboli from the wall of the conduit through the structural portion and into the lumen. Stent delivery systems capable of delivering and deploying the stent are disclosed.

7 Claims, 11 Drawing Sheets

(56) References Cited

U.S. PATENT DOCUMENTS

| | | | |
|---|---|---|---|
| 6,558,415 B2 | 5/2003 | Thompson | |
| 6,623,491 B2 | 9/2003 | Thompson | |
| 6,673,105 B1* | 1/2004 | Chen | 623/1.15 |
| 6,716,239 B2* | 4/2004 | Sowinski et al. | 623/1.13 |
| 6,800,089 B1* | 10/2004 | Wang | 623/1.44 |
| 6,814,746 B2 | 11/2004 | Thompson et al. | |
| 7,959,662 B2* | 6/2011 | Erbel et al. | 623/1.13 |
| 8,052,744 B2* | 11/2011 | Girton | 623/1.39 |
| 2002/0035394 A1* | 3/2002 | Fierens et al. | 623/1.13 |
| 2002/0038143 A1* | 3/2002 | McCrea et al. | 623/1.13 |
| 2002/0040238 A1* | 4/2002 | Rudnick et al. | 623/1.15 |
| 2002/0045931 A1* | 4/2002 | Sogard et al. | 623/1.13 |
| 2002/0082675 A1* | 6/2002 | Myers | 623/1.13 |
| 2002/0095205 A1* | 7/2002 | Edwin et al. | 623/1.13 |
| 2002/0165601 A1* | 11/2002 | Clerc | 623/1.13 |
| 2002/0178570 A1* | 12/2002 | Sogard et al. | 29/516 |
| 2003/0060871 A1* | 3/2003 | Hill et al. | 623/1.15 |
| 2003/0088308 A1* | 5/2003 | Scheuermann et al. | 623/1.15 |
| 2003/0233141 A1* | 12/2003 | Israel | 623/1.15 |
| 2004/0024448 A1* | 2/2004 | Chang et al. | 623/1.42 |
| 2004/0122509 A1* | 6/2004 | Brodeur | 623/1.34 |
| 2004/0148015 A1* | 7/2004 | Lye et al. | 623/1.15 |
| 2004/0193251 A1* | 9/2004 | Rudnick et al. | 623/1.22 |
| 2004/0215324 A1* | 10/2004 | Vonderwalde et al. | 623/1.15 |
| 2004/0220610 A1* | 11/2004 | Kreidler et al. | 606/200 |
| 2004/0236407 A1* | 11/2004 | Fierens et al. | 623/1.16 |
| 2004/0236415 A1 | 11/2004 | Thomas | |
| 2005/0070989 A1* | 3/2005 | Lye et al. | 623/1.4 |
| 2006/0142851 A1 | 6/2006 | Molaei et al. | |
| 2008/0109055 A1* | 5/2008 | Hlavka et al. | 623/1.1 |
| 2011/0125253 A1* | 5/2011 | Casanova et al. | 623/1.34 |

FOREIGN PATENT DOCUMENTS

| | | |
|---|---|---|
| WO | 2004034931 A2 | 4/2004 |
| WO | WO-2004/028340 A2 | 4/2004 |
| WO | WO-2004/034931 A2 | 4/2004 |
| WO | 2005046523 A1 | 5/2005 |
| WO | WO-2005/046523 A1 | 5/2005 |
| WO | 2006034114 A2 | 3/2006 |
| WO | WO-2006/034114 A2 | 3/2006 |
| WO | WO 2006/124549 | 11/2006 |

OTHER PUBLICATIONS

Examination Report from counterpart European Application No. 07254489.3, dated Jan. 26, 2018, 4 pp.

Examination Report from counterpart European Application No. 07254489.3, dated Aug. 31, 2018, 6 pp.

* cited by examiner

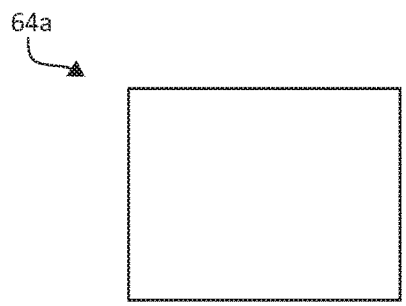
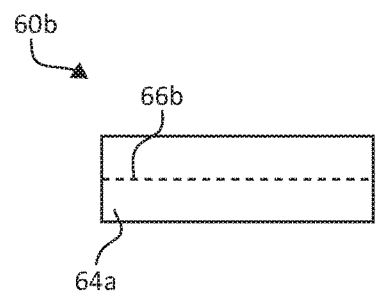
FIG. 6A  FIG. 6B
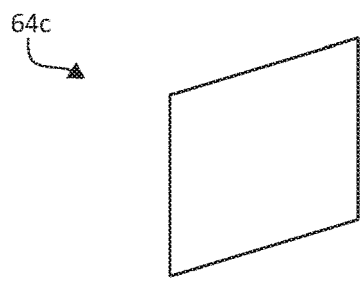
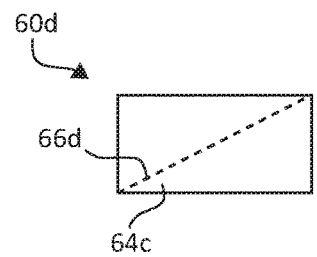
FIG. 6C  FIG. 6D
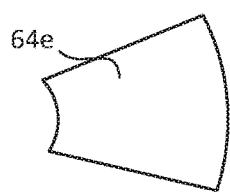
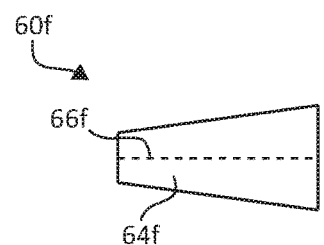
FIG. 6E  FIG. 6F
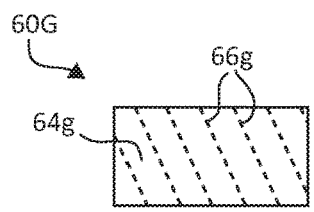
FIG. 6G

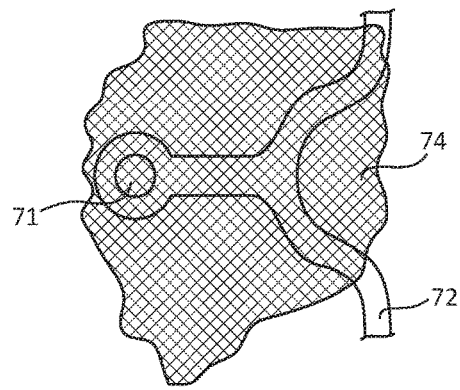
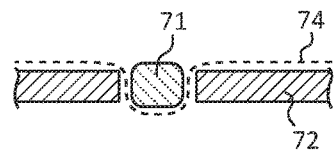
FIG. 7A
FIG. 7B
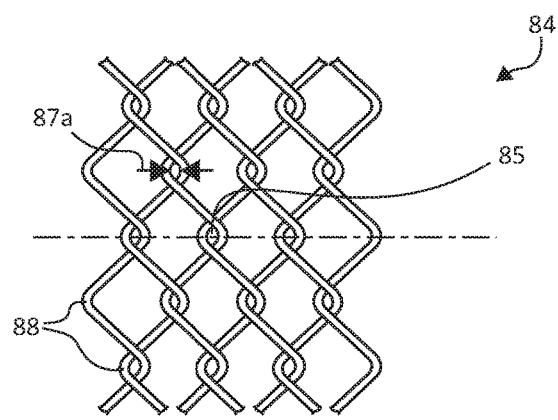
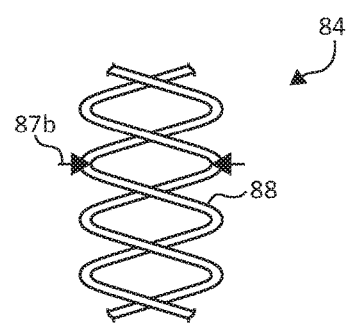
FIG. 8A
FIG. 8B

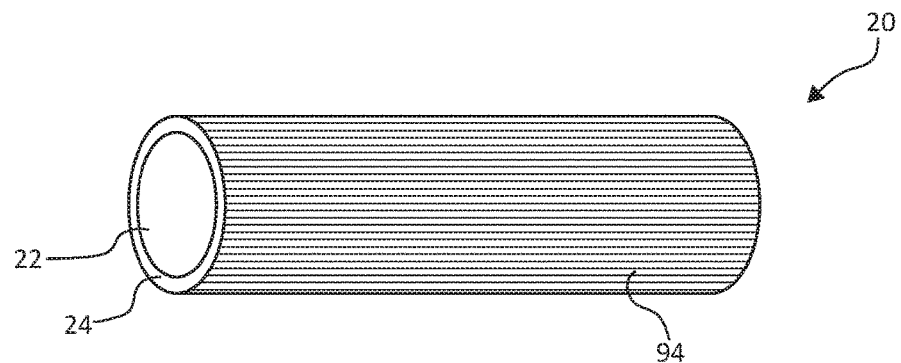
FIG. 9A
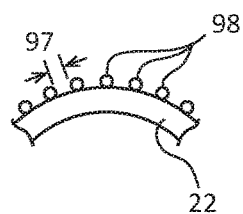
FIG. 9B
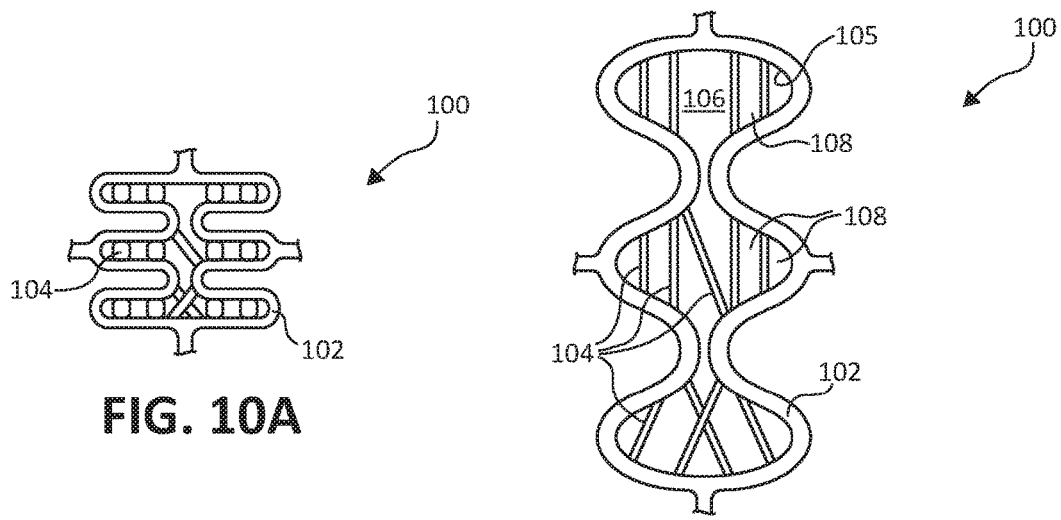
FIG. 10A
FIG. 10B

STENT HAVING REDUCED PASSAGE OF EMBOLI AND STENT DELIVERY SYSTEM

FIELD OF THE INVENTION

The present invention relates to luminal implants, and, more particularly, to stents for use in treating vascular disease.

BACKGROUND OF THE INVENTION

Stents are widely used for supporting a lumen structure in a patient's body. For example, a stent may be used to maintain patency of a carotid artery, coronary artery, other blood vessel or other body lumen such as the ureter, urethra, bronchus, esophagus, or other passage. A stent is typically a metal, tubular structure, although polymer stents are known. Stents can be permanent enduring implants, or can be bioabsorbable at least in part. Bioabsorbable stents can be polymeric, bio-polymeric, ceramic, bio-ceramic, metallic, or other materials and stents may elute over time substances such as drugs.

In certain stent designs, the stent is an open-celled tube that is expanded by an inflatable balloon at the deployment site. Another type of stent is of a "self-expanding" type. A self-expanding stent does not use a balloon or other source of force to move from a collapsed state to an expanded state. A self-expanding stent is passed through the body lumen in a collapsed state. At the point of an obstruction, or other deployment site in the body lumen, the stent is expanded to its expanded diameter for its intended purpose. An example of a self-expanding stent is a coil structure that is secured to a stent delivery device under tension in a collapsed state. At the deployment site, the coil is released so that the coil can expand to its enlarged diameter. Coil stents can be manufactured using a variety of methods, such as winding of wire, ribbon, or sheet on a mandrel or by laser cutting from a tube, followed by the appropriate heat treatments. Other types of self expanding stents are closed-cell or open-celled tubes made from a self-expanding material, for example, the Protégé GPS stent from ev3, Inc. of Plymouth, Minn. Cellular tube stents are commonly made by laser cutting of tubes, or cutting patterns into sheets followed by or preceded by welding the sheet into a tube shape, and other methods. The shape, length and other characteristics of a stent are typically chosen based on the location in which the stent will be deployed.

Conventional stents generally are comprised of struts or wires having openings therebetween. During or after stent implantation material can pass from the treatment area through the stent openings and into the lumen of the conduit being treated. This material can separate from the conduit wall, embolize into the lumen, travel downstream and cause problems. For example, atheromatous debris can extrude through stent openings into the lumen of a carotid artery, embolize into the bloodstream, and be carried downstream by blood flow until the embolus becomes lodged in a smaller vessel, causing a stroke. In a similar manner, debris can pass through stent openings in a renal artery, flow distally into the kidney, and embolize, causing impaired renal function, and debris can pass through stent openings in a sapphenous vein graft, flow distally into the myocardium, and embolize, causing impaired heart function.

Some workers in the field have added coverings to stents and thereby substantially occluded the stent openings. However, such covered stents or stent grafts, when compressed into a delivery configuration, tend to be bulky and stiff, thereby making them unsuitable for delivery to small diameter vessels or locations requiring traversal of conduit tortuosity.

Accordingly, a need exists for a stent that is small in profile and flexible when compressed into a delivery configuration and which provides appropriate vessel wall coverage to reduce passage of emboli into the lumen when deployed.

SUMMARY OF THE INVENTION

A stent for reducing the passage of emboli into body lumen once deployed includes a structural portion and a barrier portion. The structural portion, when expanded in a conduit, provides sufficient strength to maintain an open lumen in the conduit. The barrier portion reduces migration of emboli from the wall of the conduit through the structural portion and into the lumen. Stent delivery systems capable of delivering and deploying the stent are provided.

According to one aspect of the present invention, an expandable tubular stent for implantation in a body lumen comprises a structural layer extending along an axis and having a delivery diameter length and an expanded diameter length along the axis; and a barrier layer affixed to the structural layer and having a delivery diameter length and an expanded diameter length along the axis. The structural layer expanded diameter length is within the range of 1% to 25% of the barrier layer expanded diameter length.

According to a second aspect of the present invention, an expandable tubular stent for implantation in a body lumen comprises a structural layer extending along an axis and having a delivery diameter length and an expanded diameter length along the axis; and a barrier layer affixed to the structural layer and having a delivery diameter length and an expanded diameter length along the axis. The structural layer delivery diameter length being within the range of 1% to 25% of barrier layer delivery diameter length.

According to a third aspect of the present invention, an expandable tubular stent for implantation in a body lumen comprises a structural layer extending along an axis and being radially expandable from a delivery diameter to an expanded diameter about the axis; and a barrier layer affixed to the structural layer and being elastically and radially expandable from a delivery diameter to an expanded diameter about the axis. The delivery diameter of the barrier layer elastically expanding in the range of 100% to 1,500% to the barrier layer expanded diameter.

According to a fourth aspect of the present invention, an expandable tubular stent for implantation in a body lumen comprises a structural layer extending along an axis; and a barrier layer affixed to the structural layer and having a plurality of pores extending therethrough, the plurality of pores having an average pore size. The barrier layer having a range of pore sizes within ±1% to ±25% of the average pore size.

According to a fifth aspect of the present invention, an expandable tubular stent for implantation in a body lumen comprises a structural layer extending along an axis; and a barrier layer affixed to the structural layer and having a plurality of pores extending therethrough. The plurality of pores having pore sizes within a range of 40 microns to 3,000 microns.

According to a sixth aspect of the present invention, an expandable tubular stent for implantation in a body lumen comprises a structural layer extending along an axis being radially expandable thereabout and having a first expanded percentage open area; and a barrier layer affixed to the structural layer and having a second expanded percentage open area. The stent having an composite expanded percentage open area within a range of 65% to 95%.

According to a seventh aspect of the present invention, an expandable tubular stent for implantation in a body lumen comprises a structural layer extending along an axis and being radially expandable from a delivery diameter to an expanded diameter about the axis; and a barrier layer affixed to the structural layer and being plastically and radially expandable from a delivery diameter to an expanded diameter about the axis. The delivery diameter of the barrier layer plastically expanding in the range of 100% to 1,500% to the barrier layer expanded diameter.

BRIEF DESCRIPTION OF THE DRAWINGS

The above and further advantages of the invention may be better understood by referring to the following description in conjunction with the accompanying drawings in which:

FIGS. 6A, 6B, 6C, 6D, 6E, 6F, and 6G illustrate conceptually portions of stents in accordance with the present invention;

FIGS. 7A and 7B illustrate conceptually portions of stents in accordance with the present invention;

FIGS. 8A and 8B illustrate conceptually portions of stents in accordance with the present invention;

FIGS. 9A and 9B illustrate conceptually portions of stents in accordance with the present invention;

FIGS. 10A and 10B illustrate conceptually stents in accordance with the present invention;

DETAILED DESCRIPTION

Figure 1:
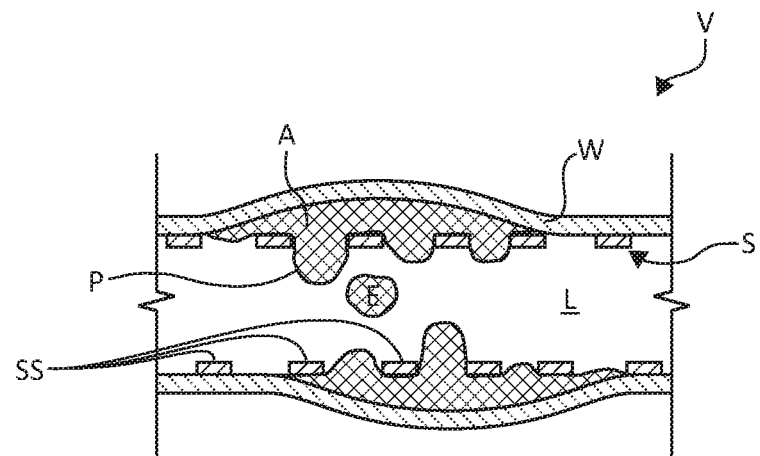
FIG. 1 illustrates conceptually a partial cross-sectional diagram of a prior art stent deployed in a conduit.

FIG. 1 illustrates a prior art stent deployed in a conduit. Vessel V having vessel wall W and lumen L has stent S expanded within lumen of vessel. Previous treatment by dilation of vessel lumen L has caused atheroma A to be expanded from a position where vessel lumen L was narrowed by the atheroma (not shown) to a position where atheroma no longer blocks passage of fluid through lumen L. Dilation of atheroma A has caused vessel wall W to be expanded in the vicinity of atheroma and stent S has been deployed in the vicinity of atheroma to maintain expanded diameter of lumen L. Due to the elasticity of vessel wall W a radially contractile force is exerted on atheroma A, causing pillows P of atheroma to extrude between stent struts SS. In some cases pillows P of atheroma A become detached and form emboli E which travel downstream in lumen L.

Figure 2:
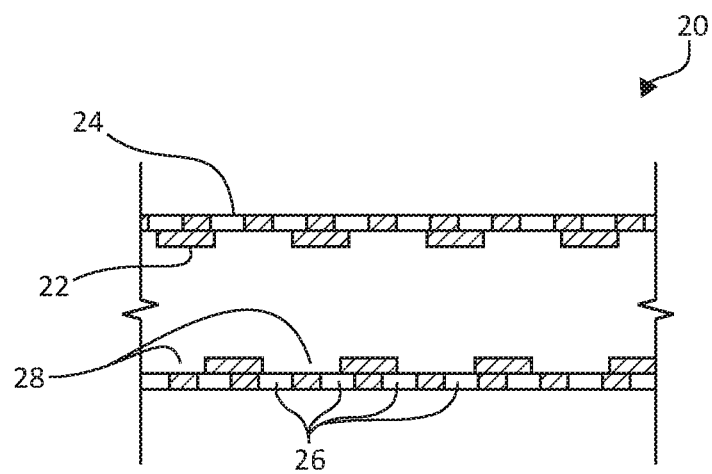
FIG. 2 illustrates conceptually a partial cross-sectional diagram of an expanded stent in accordance with the present invention.

FIG. 2 illustrates an expanded stent in accordance with the present invention. Stent 20 has a delivery diameter and an expanded diameter and is comprised of structural portion 22 and barrier portion 24. Structural portion, when expanded in a conduit, provides sufficient strength to maintain an open lumen in the conduit, in part by providing sufficient radial strength, kink resistance, and fatigue resistance. Structural portion may be comprised of known stent designs and may be balloon expandable or self expanding. Suitable stent designs include but are not limited to those described in U.S. Pat. No. 6,558,415 "Stent", U.S. Pat. No. 6,358,274 "Stent", U.S. patent application Ser. No. 60/840,170 "Implant Having High Fatigue Resistance, Delivery System, and Method of Use" and U.S. patent application Ser. No. 60/800,106 "Implant and Delivery System with Multiple Marker Interlocks", the contents of which being incorporated in their entirety herein by reference. Barrier portion 24 reduces migration of emboli from the wall of the conduit through the structural portion and into the lumen in part by providing pores 26 which may be smaller in size than openings 28 in structural portion 22.

Stent 20 delivery diameter is the diameter of stent 20 when loaded into a stent delivery system and stent expanded diameter is the diameter of stent 20 when deployed in the lumen of a conduit. It is known for structural portions and barrier portions to lengthen or shorten when expanded from delivery diameter to expanded diameter. For stents 20 having structural portions and barrier portions that may be bonded together it is important that the two portions have similar lengths when in the expanded diameter so that shear stresses are not present at the interface between the two portions. Excessive shear stresses at this interface can contribute to failure of the interface on deployment or over time due to fatigue and subsequent debonding of the portions. Similarly, for stents 20 having structural portions and barrier portions that may be bonded together it is important that the two portions have similar lengths when in the delivery diameter so that shear stresses are not present at the interface between the two portions. Excessive shear stresses at this interface can contribute to failure of the interface over time in storage and subsequent debonding of the portions leading to stent 20 deployment difficulties.

Structural portion expanded diameter length can be measured by constraining the structural portion at the same diameter as it has when stent 20 is in the stent expanded diameter; similarly barrier portion expanded diameter length can be measured by constraining the barrier portion at the same diameter as it has when stent 20 is in the stent expanded diameter. Structural portion expanded diameter lengths within 1% to within 25% of barrier portion expanded diameter lengths are contemplated. In one embodiment, structural portion expanded diameter length is within 25% of barrier portion expanded diameter length. In another embodiment, structural portion expanded diameter length is within 15% of barrier portion expanded diameter length. In another embodiment, structural portion expanded diameter length is within 10% of barrier portion expanded diameter length. In another embodiment, structural portion expanded diameter length is within 5% of barrier portion expanded diameter length. In another embodiment, structural portion expanded diameter length is within 2.5% of barrier portion expanded diameter length.

Structural portion delivery diameter length can be measured by constraining the structural portion at the same diameter as it has when stent 20 is in the stent delivery diameter; similarly barrier portion delivery diameter length can be measured by constraining the barrier portion at the same diameter as it has when stent 20 is in the stent delivery diameter. Also, structural portion expanded diameter lengths within 1% to within 25% of barrier portion expanded diameter lengths and structural portion delivery diameter lengths within 1% to within 25% of barrier portion delivery diameter lengths are contemplated. In yet another embodiment, structural portion expanded diameter length is within 25% of barrier portion expanded diameter length and structural portion delivery diameter length is within 25% of barrier portion delivery diameter length. In another embodiment, structural portion expanded diameter length is within 15% of barrier portion expanded diameter length and structural portion delivery diameter length is within 15% of barrier portion delivery diameter length. In another embodiment, structural portion expanded diameter length is within 10% of barrier portion expanded diameter length and structural portion delivery diameter length is within 10% of barrier portion delivery diameter length. In another embodiment, structural portion expanded diameter length is within 5% of barrier portion expanded diameter length and structural portion delivery diameter length is within 5% of barrier portion delivery diameter length. In another embodiment, structural portion expanded diameter length is within 2.5% of barrier portion expanded diameter length and structural portion delivery diameter length is within 2.5% of barrier portion delivery diameter length.

In some embodiments, barrier portion 24 elastically expands from barrier portion delivery diameter to barrier portion expanded diameter, thereby eliminating the need to fold or deform barrier portion 24 during deployment and expansion of stent 20. Folds in barrier portion 24 at the delivery diameter increase effective thickness of barrier portion 24 and thereby crossing profile of stent 20 when in the stent delivery diameter. Deformation of barrier portion 24 during stent 20 expansion carry's the risk that barrier portion 24 will be torn during expansion, increases force needed to deploy stent 20, and decreases ability to recover stent 20 prior to full deployment of stent 20. In some embodiments, stent 20 having a delivery diameter of 1 mm is deployed in a vessel having a diameter of 5 mm or more, requiring at least a 500% radial expansion of barrier. Barrier portion elastic expansions from delivery diameter to expanded diameter of 100% to 1,500% are contemplated. In one embodiment, barrier portion elastic expansion from delivery diameter to expanded diameter is greater than 100%. In another embodiment, barrier portion elastic expansion from delivery diameter to expanded diameter is greater than 250%. In another embodiment, barrier portion elastic expansion from delivery diameter to expanded diameter is greater than 500%. In another embodiment, barrier portion elastic expansion from delivery diameter to expanded diameter is greater than 750%. In another embodiment, barrier portion elastic expansion from delivery diameter to expanded diameter is greater than 1,000%.

In some embodiments barrier portion 24 radially expands from barrier portion delivery diameter to barrier portion expanded diameter by a combination of elastic and plastic deformations during deployment and expansion of stent 20. This mode of expansion is particularly applicable for balloon expandable stents, where the motive expansile force provided by the balloon can overcome the barrier portion resistance to radial expansion. In some embodiments, stent 20 having a delivery diameter of 1 mm is deployed in a vessel having a diameter of 5 mm or more, requiring at least a 500% radial expansion of barrier. Barrier portion plastic deformations from delivery diameter to expanded diameter of 100% to 1,500% are contemplated. In one embodiment, barrier portion plastic deformation from delivery diameter to expanded diameter is greater than 100%. In another embodiment, barrier portion plastic deformation from delivery diameter to expanded diameter is greater than 250%. In another embodiment, barrier portion plastic deformation from delivery diameter to expanded diameter is greater than 500%. In another embodiment, barrier portion plastic deformation from delivery diameter to expanded diameter is greater than 750%. In another embodiment, barrier portion plastic deformation from delivery diameter to expanded diameter is greater than 1,000%.

Barrier portion 24 is comprised of pores 26. Pores may be sufficiently small to prevent atheroma from traversing barrier portion 24 through pores 26 and subsequent embolization into distal tissues. The size of embolus that must be prevented is related to the anatomy of downstream tissue beds within which the embolus will lodge. For example, it is known that large emboli, on the order of 1,000 microns in diameter, can occlude branch arteries resulting in ischemia to the tissue supplied with blood by the artery. Small emboli, on the order of 50 microns in diameter, can occlude retinal arteries resulting in ischemia to the eye and at least partial blindness.

Figure 3A:
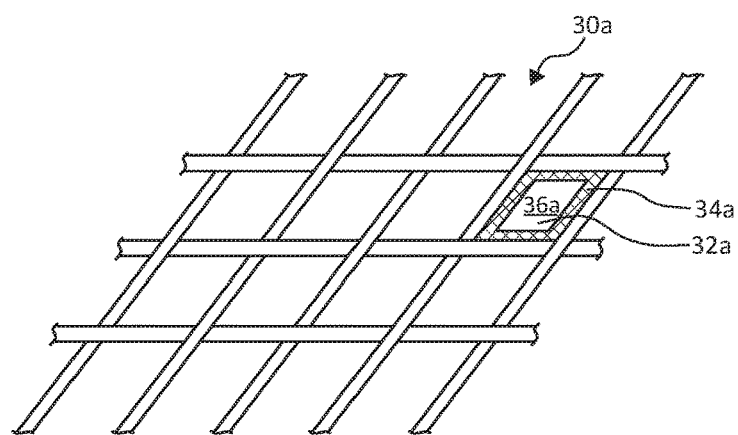
FIGS. 3A, 3B, and 3C illustrate conceptually a portion of a stent in accordance with the present invention.
Figure 3B:
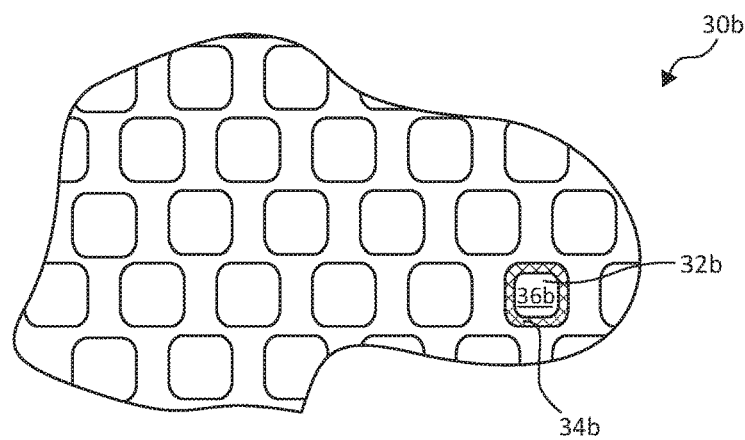
Figure 3C:
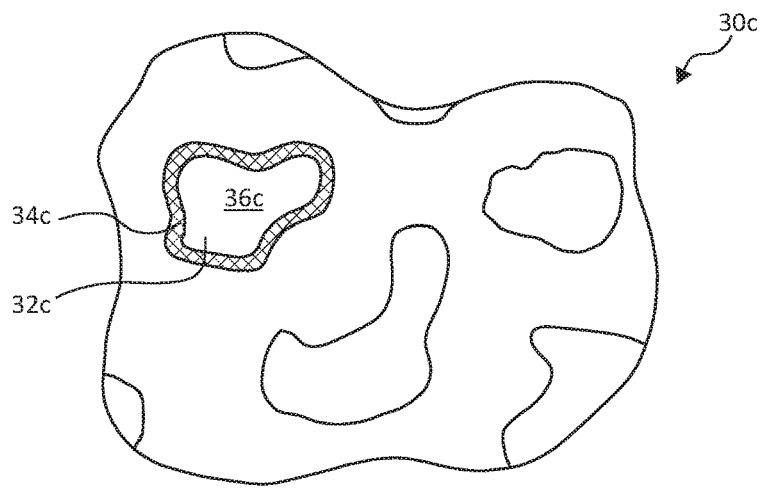

Pore size can be characterized as equal to the diameter of a circle having the same area as the area bounded by the perimeter of a pore. FIGS. 3A, 3B, and 3C illustrate portions of barrier portions 30*a*, 30*b*, and 30*c* having pores 32*a*, 32*b*, and 32*c* of various shapes. The pores 32*a*, 32*b*, and 32*c* have perimeters (illustrated by bolded line in the figures) 34*a*, 34*b*, and 34*c* and area's 36*a*, 36*b*, and 36*c* enclosed by perimeters 34*a*, 34*b*, and 34*c* respectively. Barrier portion 30*a* is comprised of interwoven filaments, barrier portion 30*b* is comprised of a film, in some embodiments a polymer film, having regularly spaced openings extending through the thickness of the film, and barrier portion 30*c* is comprised of a film, in some embodiments a cast polymer film, having irregularly spaced openings extending through the thickness of the film.

For all of the barrier portions having pores within the scope of this invention one can calculate an average pore size and a range of pore sizes using established statistical techniques. Barrier portion pore sizes of 40 microns to 3,000 microns, and barrier portion range of pore sizes within ±25% of the average pore size to within ±1% of the average pore size are contemplated. In one embodiment, barrier portion has a pore size of 2,500 microns. In another embodiment, barrier portion has a pore size of 1,500 microns. In another embodiment, barrier portion has a pore size of 1,000 microns. In another embodiment, barrier portion has a pore size of 750 microns. In another embodiment, barrier portion has a pore size of 500 microns. In another embodiment, barrier portion has a pore size of 250 microns. In another embodiment, barrier portion has a pore size of 125 microns. In another embodiment, barrier portion has a pore size of less than 80 microns. In yet another embodiment, barrier portion has a range of pore sizes within ±25% of the average pore size. In another embodiment, barrier portion has a range of pore sizes within ±15% of the average pore size. In another embodiment, barrier portion has a range of pore sizes within ±10% of the average pore size. In another embodiment, barrier portion has a range of pore sizes within ±5% of the average pore size.

Figure 4A:
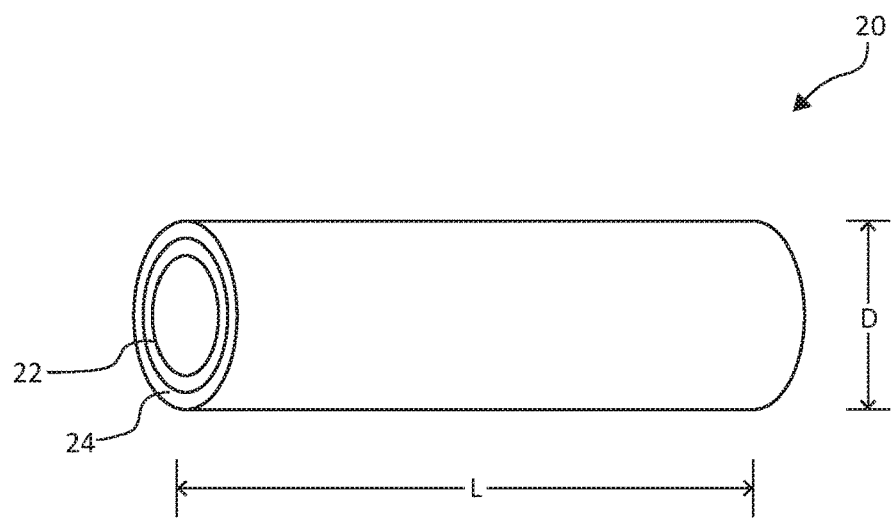
FIGS. 4A and 4B illustrate conceptually isometric or partial cross-sectional diagrams of an expanded stent in accordance with the present invention.
Figure 4B:
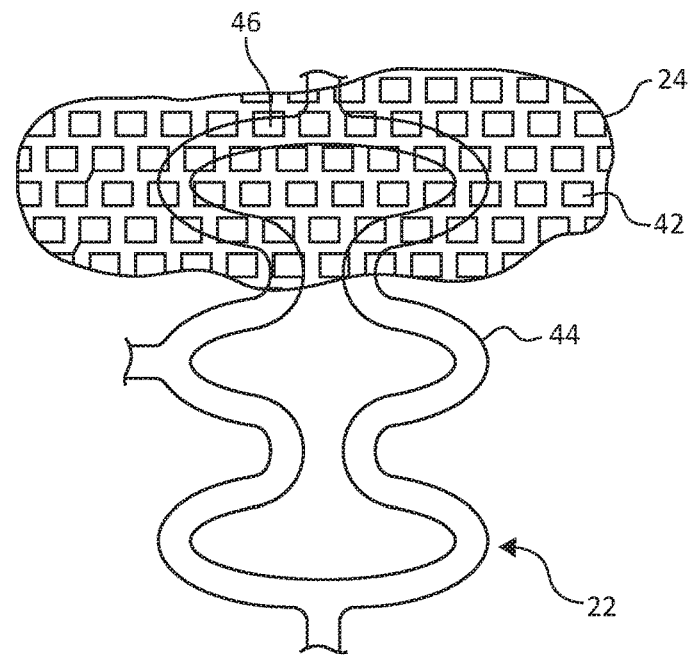

Stents 20 in accordance with the present invention have a percentage open area when expanded. With reference to FIGS. 4A and 4B, the percentage open area of stent 20 is defined as the (area of barrier portion 24 pores 42 minus the area of barrier portion pores occluded by structural portion 22 struts 44, for example, pore 46) all divided by the surface area of expanded stent 20 (defined as length of expanded stent L times diameter of expanded stent D times 3.14). Expanded stent percentage open areas of 65% to 95% are contemplated. In one embodiment, expanded stent percentage open area is 70%. In another embodiment, expanded stent percentage open area is 75%. In another embodiment, expanded stent percentage open area is 80%. In another embodiment, expanded stent percentage open area is 85%. In another embodiment, expanded stent percentage open area is 90%.

Figure 5A:
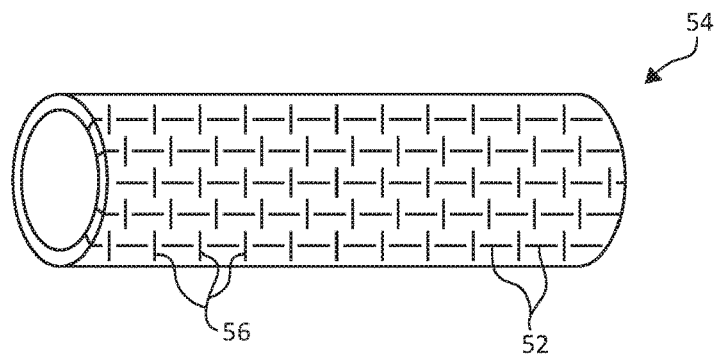
FIGS. 5A, 5B, and 5C illustrate conceptually portions of stents in accordance with the present invention.
Figure 5B:
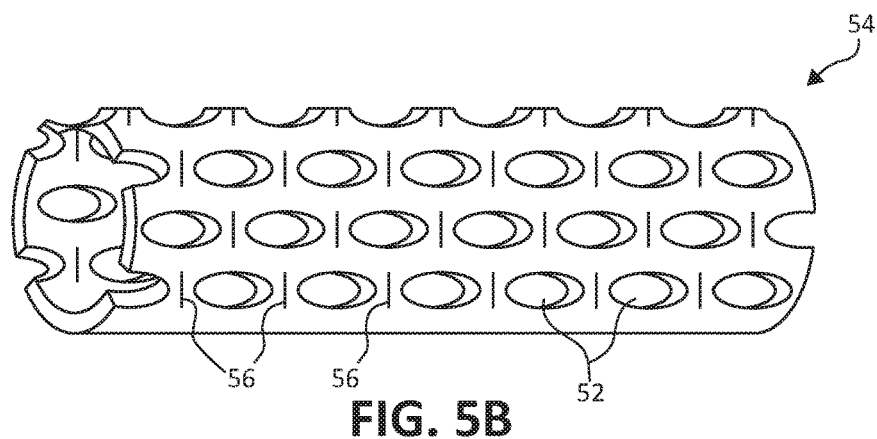
Figure 5C:
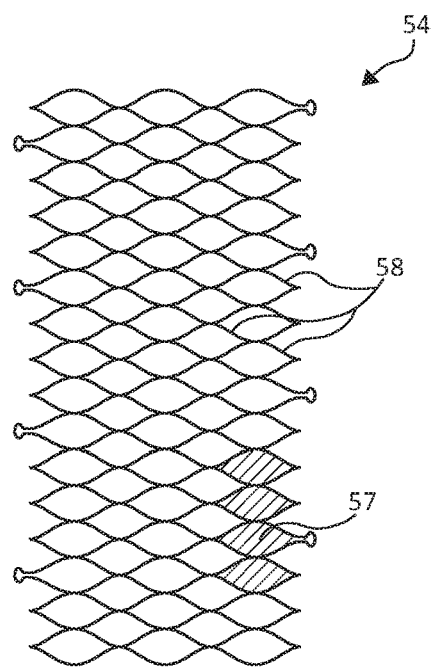

Several examples of suitable barrier portions are now described. FIG. 5A illustrates tubular barrier portion 54 in a delivery diameter comprised of a sheet or film of material having lines of weakness 52, 56. Lines of weakness 52 open to form pores when barrier portion 54 is expanded (FIG. 5B). Tubular barrier portion can be made by etching, cutting, electrodeposition onto a substrate or removable mandrel, physical deposition onto a substrate or removable mandrel, casting, or other methods. Lines of weakness 56 provide bending flexibility about longitudinal axis of barrier portion. In one example, shown expanded in FIG. 5C, barrier portion 54 is comprised of connected cellular elements 57 having struts 58.

Barrier portion sheet or film may be comprised of metal including but not limited to Nitinol, stainless steel, gold, platinum, and cobalt-chromium alloy; or polymer including but not limited to ePTFE, polyurethane, polycarbonate urethane, polyethylene, polyethylene oxide, silicone, oriented polymer films made from material such as polyester, polylactic acid, and polyglycolic acid. Lines of weakness may be partial thickness of through thickness cuts, openings, slits, slots, perforations, thinned regions, laser cut holes, or other zones that will form an opening when expanded from delivery diameter to expanded diameter. Barrier portion thicknesses between 0.0002" and 0.005" are contemplated. In one example, barrier portion thickness is 0.0005". In another example, barrier portion thickness is 0.001". In another example, barrier portion thickness is 0.0015". In another example, barrier portion thickness is 0.002". In another example, barrier portion thickness is 0.003".

Lines of weakness in barrier portion sheet or film may be made by laser cutting, chemical etching, stamping, cutting, piercing, laser drilling, or other means. In one embodiment, a barrier portion sheet or film having lines of weakness is made by electroforming on a mold and removing the mold. In another embodiment, a barrier portion sheet or film having lines of weakness is made by casting a mixture of polymer and dissolvable salts followed by removal of cast-in dissolvable elements.

Barrier portion 54 may be comprised of a tubular shape as illustrated in FIGS. 5A-5B. When assembled onto structural portion 22 tubular shape barrier portion 54 has high reliability and low cost because the assembly requires no seam(s) in the barrier portion. Barrier portion may also be comprised of flat sheet or ribbon shapes as illustrated in FIGS. 6A-6G. FIG. 6A illustrates barrier portion 64a comprised of a rectangular shape, and FIG. 6B illustrates stent 60b comprised of barrier portion 64a assembled onto structural portion 22 (not shown) and having seam 66b. FIG. 6C illustrates barrier portion 64c comprised of a parallelogram shape, and FIG. 6D illustrates stent 60d comprised of barrier portion 64c assembled onto structural portion 22 (not shown) and having seam 66d. FIG. 6E illustrates barrier portion 64e comprised of an irregular shape, and FIG. 6F illustrates tapered stent 60f comprised of barrier portion 64e assembled onto structural portion 22 (not shown) and having seam 66f. FIG. 6G illustrates stent 60g comprised of ribbon shaped barrier portion 64g assembled onto structural portion 22 (not shown) and having seam 66g. For any of these configurations the barrier portion can extend over all of or over a portion of the length of structural portion 22. In one embodiment, the barrier portion extends over the central portion only of structural portion and the ends of structural portion may be not covered by barrier.

Barrier portion 64a, 64c, 64e, 64g seams 66b, 66d, 66f, 66g can be made by adhesive bonding (where barrier portions at least partially overlap), adhesive bridging (where barrier portions do not overlap), heat bonding, welding, solvent bonding, mechanical interlock, and other methods.

Barrier portions 24, 30a, 30b, 30c, 54, 64a, 64c, 64e, 64g, and others in the shape of tubes, sheets, films, strips, or other shapes can be attached to structural portion 22 in a variety of ways. Barrier portions can be adhesively bonded, solvent bonded, soldered, brazed, welded, sintered, mechanically interlocked, fused, tied, overmolded, thermoformed, or otherwise fixedly or slideably attached. Adhesive bonding can be accomplished with or without use of primers or bonding layers. Biologically active materials may be incorporated into the bonding substances and release kinetics of the biologically active materials can be tailored to the anatomical site and to the disease being treated. For example, bonding layers may comprise sirolimus, ABT-578, zotarolimus, tacrolimus, picrolimus, pimecrolimus, everolimus, biolimus A 9, paclitaxel, analogs to these drugs, estrogens (including 17 B Estradiol), Progesterone, anticoagulants, heparinoids, anti-restenotic drugs, steroids, immunosuppressants, anti-inflammatory drugs, antineoplastic drugs, and other drugs. Barrier portion can be attached to structural portion 22 at one or both ends only, at discrete points along the length of the barrier, over some or all of the length of the barrier, over some or all of the circumference of the barrier, or at other regions. Barrier portion may be unattached to structural portion 22, and barrier portion may be self contracting in relation to structural portion so as to effect a compressive force onto some or all of structural portion 22. In one embodiment, ends of barrier portion and structural portion may be successively dipped into a cleaning solution, a flux, a soldering paste, and a salt bath to effect a soldered connection between barrier portion and structural portion. In another embodiment, structural portion is coated with gold brazing alloy, barrier portion is brought into contact with brazing alloy, and heat is applied so as to braze the portions together. In another embodiment the amount and characteristics of the brazing alloy and the processing conditions may be adjusted to prevent flow of brazing alloy into pores of barrier portion except for in pores adjacent to structural portion. In yet another embodiment, solder mask or temperature control is used to prevent flow of solders into some regions of barrier portion.

To assist with attachment of barrier portion to structural portion, structural portion may be provided with tabs, protrusions, surface roughness, or other structure to enhance or provide mechanical attachment of the 2 layers. Structural portion, barrier portion, or both may be provided with attachment zones that provide for enhanced attachment of the portions at one or more regions along their length or circumference. Attachment zones or other means may be used to register the alignment of barrier portion relative to structural portion so as to effect desired characteristics of expansion, flexibility, radiopacity, or other characteristics. In one embodiment (FIGS. 7A and 7B) barrier portion 74 is mechanically interlocked to structural portion 72 by rivet 71. Rivet may be comprised of metal, polymer, or other material and is fixedly attached to structural portion 72 by frictional forces. Rivet 71 may be comprised of radiopaque materials including gold, platinum, tungsten, and other materials. In some embodiments rivet 71, as illustrated in FIG. 7A, may have cross sectional shapes other than circular, including but not limited to square, rectangular, ovoid, and elliptical.

Barrier portion can be attached to structural portion using degradable materials including polylactic acid, polyglycolic acid, polyethylene oxide, and other materials. Biologically active materials may be incorporated into the degradable materials and release kinetics of the biologically active materials can be tailored to the anatomical site and to the disease being treated. For example, barrier portions may comprise sirolimus, ABT-578, zotarolimus, tacrolimus, picrolimus, pimecrolimus, everolimus, biolimus A 9, paclitaxel, analogs to these drugs, estrogens (including 17 B Estradiol), Progesterone, anticoagulants, heparinoids, antirestenotic drugs, steroids, immunosuppressants, anti-inflammatory drugs, antineoplastic drugs, and other drugs. Barrier portion may also be comprised of a coating of biodegradable polymer, drugs including those listed above, or both. Barrier portion may comprise surfaces conducive to cellular overgrowth or cellular attachment or both. In one embodiment barrier portion is comprised of a coating of bioadhesive polyphenolic proteins suitable for use as a cell attachment factor such as collagen, chondroitin sulfate A, fibronectin, gelatin, laminin, vitronectin, and the like. In another embodiment barrier portion is comprised of micromachined or etched surface structure having a porous layer comprised of openings in the range of 5-30 microns.

Barrier layers can be sandwiched between 2 or more structural layers and any of the 2 or more layers may be registered relative to one another to effect desired characteristics of expansion, flexibility, radiopacity, or other characteristics. Structural layers can be sandwiched between 2 or more barrier layers and any of the 2 or more layers may be registered relative to one another to effect desired characteristics of expansion, flexibility, radiopacity, or other characteristics.

Barrier portion may be comprised of interwoven filaments in forms such as braids, knits, chain link; may be comprised of non-woven fiber mats or felts; or may have other filamentous structures. Filaments may be comprised of metals such as stainless steel, Nitinol, cobalt chrome alloy, platinum, gold, or other metals; may be comprised of polymers such as polyethylene, polyurethane, silicone, polyglycolic acid, polylactic acid, cellulose, collagen, or may be comprised of other materials. Fibers may be produced by spinning, electrospinning, drawing, extrusion, epitaxial growth, or other means, and may be prepared in bulk for later attachment to structural member or may be applied directly to structural member as part of the process for forming the fibers. In one embodiment barrier portion 84 is comprised of filaments 88 woven into a chain link structure having axis 85. FIG. 8A illustrates barrier portion 84 in expanded configuration having filament spacings 87a at filament bend points and FIG. 8B illustrates barrier portion 84 in contracted configuration having filament spacings 87b at filament bend points (for clarity, only a portion of filaments are illustrated in FIG. 8B). Filament spacings 87b may be greater than filament spacings 87a, and due in part to this aspect of barrier portion 84 it is possible to greatly contract barrier portion 84 in a direction normal to axis 85 with little or no length change in a direction parallel to axis 85. In one embodiment barrier portion 84 is woven from metal filaments on a braiding machine and barrier portion 84 is attached to structural portion 22 with axis 85 oriented parallel to axis of structural portion. In another embodiment barrier portion 84 is woven from metal filaments on a braiding machine and barrier portion 84 is attached to structural portion 22 with axis 85 oriented normal to axis of structural portion.

In another embodiment (FIGS. 9A and 9B) stent 90 comprises barrier portion 94 having linear filaments 98 attached to surface of structural portion 22. filaments 98 may be oriented parallel to axis of stent 90 or may be oriented at an angle relative to axis of stent 90. Filaments 98 may be separated by gap 97 when stent is expanded. Gap allows stent 90 to be contracted into a delivery diameter without dislodging filaments from surface of structural member. In one embodiment filaments have a diameter of 25 microns and gap equals 100 microns when stent 90 is at a maximum expanded diameter.

Barrier portion can be comprised of bridges of material attached to stent structural portion. FIGS. 10A and 10B illustrate stent 100 comprised of structural portion 102 and barrier portion 104. Structural portion 102 is comprised of cells 106 having perimeter 105. Barrier portion 104 is comprised of elasticly or plasticly deformable material attached at 2 or more places along perimeter of structural portion. Barrier portion 104 may be comprised of metals such as stainless steel, Nitinol, cobalt chrome alloy, platinum, gold, or other metals; may be comprised of polymers such as polyethylene, polyurethane, silicone, polyglycolic acid, polylactic acid, cellulose, collagen, or may be comprised of other materials. In FIG. 10A stent 100 is illustrated in an unexpanded configuration, for example in a delivery configuration, and barrier portion has a short length that spans the open space in cell 106. In FIG. 10B stent 100 is illustrated in an expanded configuration, for example in an implanted configuration, and barrier portion has a longer length than in FIG. 10A that spans the open space in cell 106. Barrier portions 104 together with perimeter of structural portion cells 106 form pores 108 in stent 100. In another embodiment some or all of structural portion cell 106 is filled with polymer material attached to cell perimeter 105. Expansion of structural portion 102 causes polymer portion to fracture yet remain attached to perimeter 105, thereby creating pores 108 at polymer fracture sites.

Figure 11A:
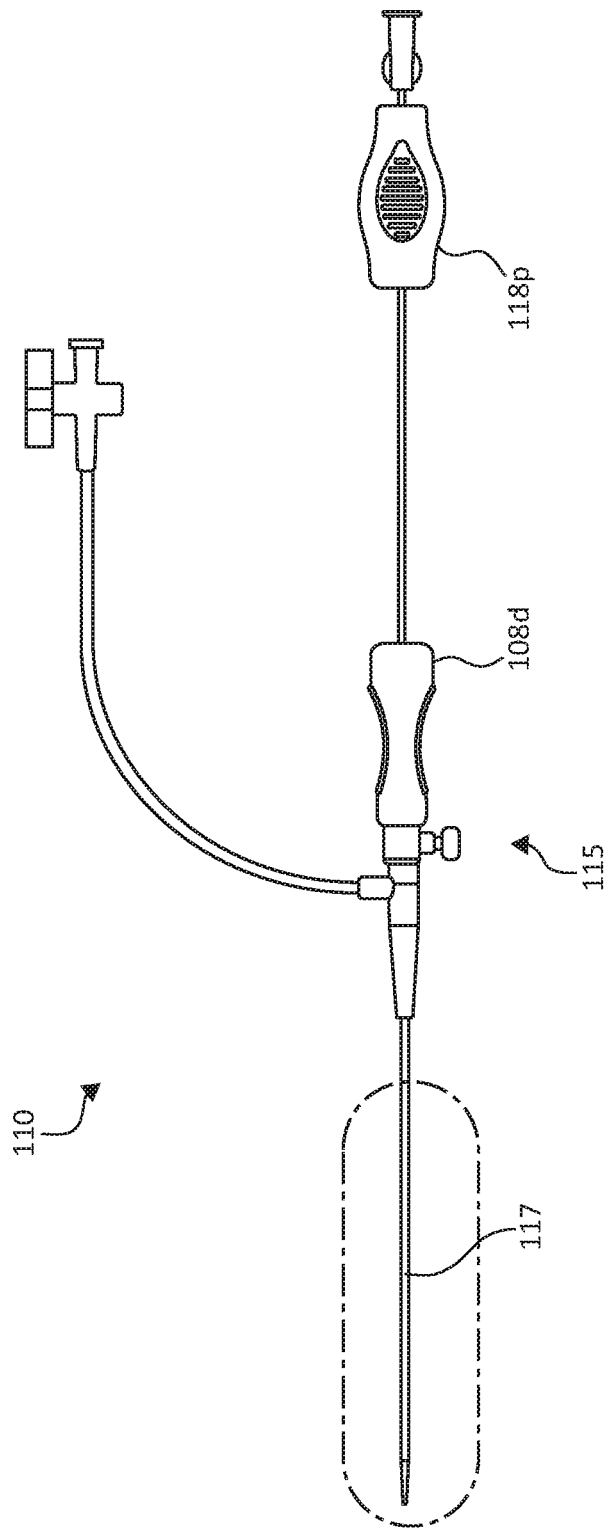
FIGS. 11A, 11B, and 11C illustrate conceptually one example of an OTW stent delivery system in accordance with the present invention.
Figure 11B:
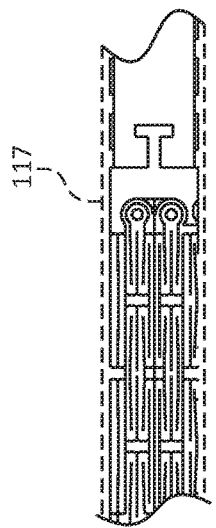
Figure 11B:
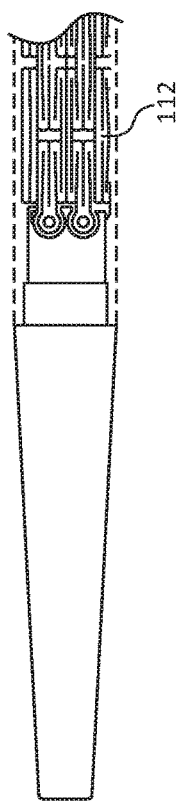
Figure 11C:
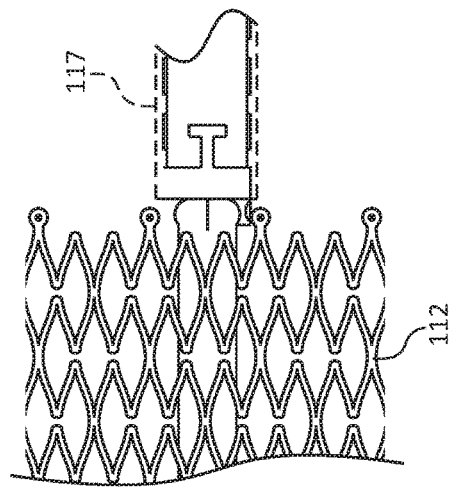
Figure 11C:
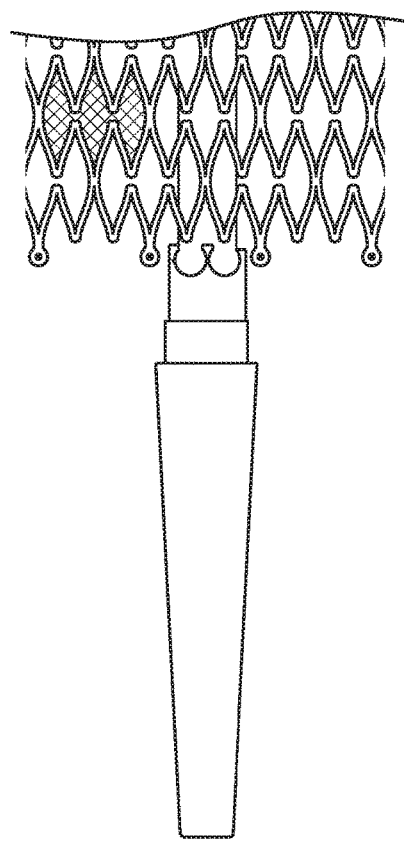
Figure 12A:
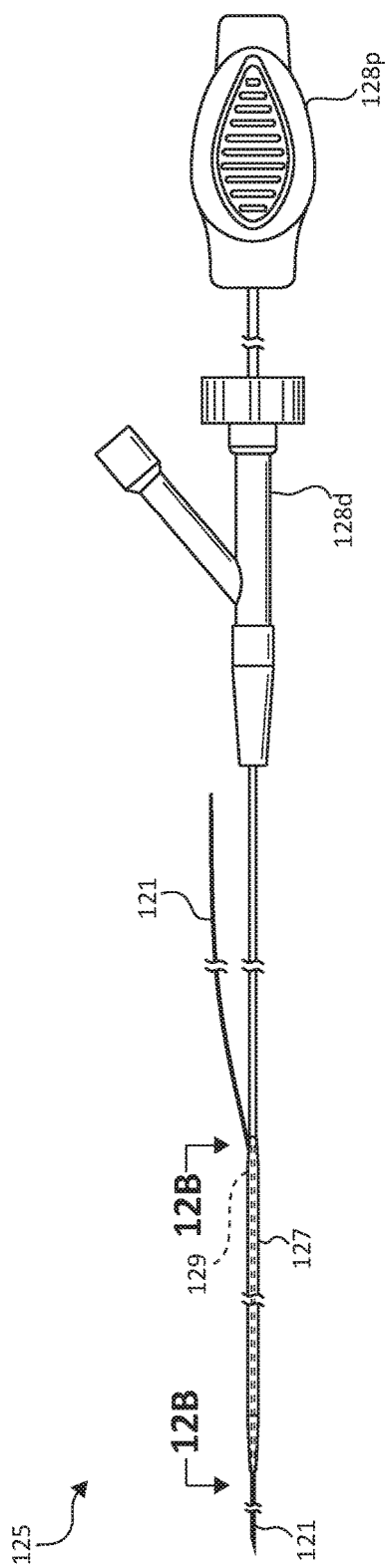
FIGS. 12A and 12B illustrate conceptually one example of an RX stent delivery system in accordance with the present invention.
Figure 12B:
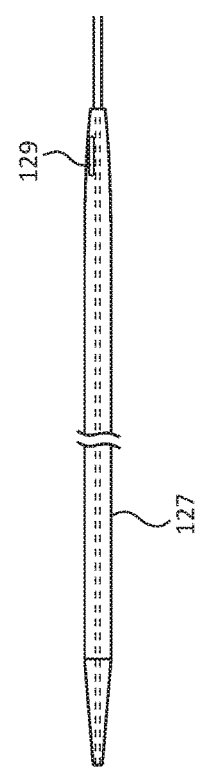
Figure 13:
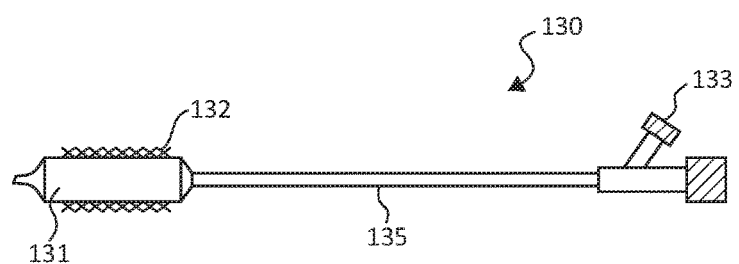
FIG. 13 illustrates conceptually one example of an OTW stent delivery system in accordance with the present invention.
Figure 14:
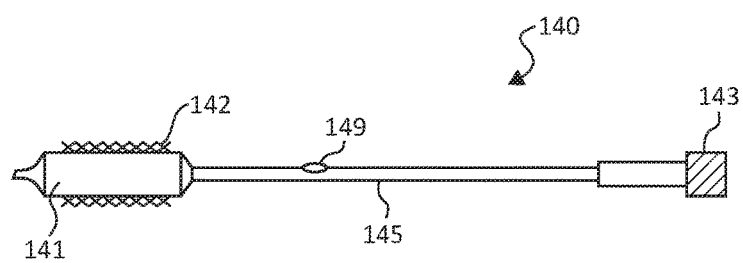
FIG. 14 illustrates conceptually one example of an RX stent delivery system in accordance with the present invention.

Delivery systems suitable for a stent having reduced passage of emboli into a lumen when deployed may be comprised of over-the wire (OTW) and rapid exchange (RX) systems. FIGS. 11A, 11B and 11C illustrate one example of an OTW delivery system 110 comprised of self expanding stent 112 having reduced passage of emboli and self expanding stent delivery catheter 115 comprised of sheath 117, proximal handle 118p and distal handle 118d. Stent 112 is deployed by sliding handles closer together, thereby withdrawing sheath 117 proximally and uncovering stent 112, allowing stent to self-expand. FIGS. 11A and 11B illustrate stent 112 in an unexpanded delivery configuration and FIG. 11C illustrates stent 112 in an expanded deployed configuration. FIGS. 12A and 12B illustrate one example of an RX delivery system comprised of self expanding stent 122 having reduced passage of emboli (not shown) within lumen of sheath and self expanding stent delivery catheter 125 comprised of sheath 127, guidewire exit skive 129, guidewire 121, proximal handle 128p and distal manifold 128d. Stent 122 is deployed by sliding proximal handle 128p and distal manifold 128d closer together, thereby withdrawing sheath 127 proximally and uncovering stent 122, allowing stent to self-expand. FIG. 13 illustrates one example of an OTW delivery system 130 comprised of balloon expandable stent 132 having reduced passage of emboli in a partially expanded configuration, catheter shaft 135 having balloon inflation lumen (not shown), balloon 131, and inflation hub 133. Stent 132 is deployed by connecting inflation device (not shown) to hub 133 and pressurizing catheter lumen with fluid or gas so as to expand balloon 131 thereby expanding stent 132. FIG. 14 illustrates one example of an RX delivery system 140 comprised of balloon expandable stent 142 having reduced passage of emboli in a partially expanded configuration, catheter shaft 145 having balloon inflation lumen (not shown), guidewire exit skive 149 in catheter shaft 145, balloon 141, and inflation hub 143. Stent 142 is deployed by connecting inflation device (not shown) to hub 143 and pressurizing catheter lumen with fluid or gas so as to expand balloon 141 thereby expanding stent 142. Suitable stent delivery catheter designs include but are not limited to those described in U.S. Pat. No. 6,814,746 "Implant Delivery System With Marker Interlock", U.S. Pat. No. 6,623,491 "Stent Delivery System with Spacer Member", Patent Application No. PCT/US2006/018356 "Implant Delivery System With Interlocked Rx Port Orientation" and U.S. patent application Ser. No. 60/800,106 "Implant and Delivery System with Multiple Marker Interlocks", the contents of which being incorporated in their entirety herein by reference.

An exemplary method of using a stent having reduced passage of emboli into a lumen when deployed is now described. A guidewire is advanced into a patient's femoral artery using known techniques, through a patient's vessel and past a treatment site. An inventive stent (for example stent 122) is loaded onto a stent delivery system (for example, system 125) and introduced over the guidewire into the patient's vessel. The stent and stent delivery system combination is advanced over the guidewire and through the patients vessel until the stent is located at a treatment site, for example within a stenosis in a carotid artery. Stent 122 is deployed by sliding proximal handle 128p and distal manifold 128d closer together, thereby withdrawing sheath 127 proximally and uncovering stent 122, allowing stent to self-expand. In some embodiments, before the sheath is completely withdrawn from the stent an operator can advance the sheath distally so as to recapture the stent. This is possible because the barrier portion provides a smooth covering over the structural portion of the stent so that the distal end of the sheath will not become mechanically entangled with the structural portion. Recapture of a stent is desirable when the operator wishes to change the eventual deployed position of the stent or for other reasons. Stent delivery system 125 is then withdrawn through the patient's vessel and out of the patient's body.

Another exemplary method of using a stent having reduced passage of emboli into a lumen when deployed is now described. A guidewire is advance into a patient's femoral artery using known techniques, through a patient's vessel and past a treatment site. An inventive stent (for example stent 132) is loaded onto a stent delivery system (for example, system 130) and introduced over the guidewire into the patient's vessel. The stent and stent delivery system combination is advanced over the guidewire and through the patients vessel until the stent is located at a treatment site, for example within a stenosis in a carotid artery. Stent 132 is deployed by inflating balloon 131 thereby causing stent to expand. Stent delivery system 135 is then withdrawn through the patient's vessel and out of the patient's body.

While this document has described an invention mainly in relation to vascular stenting, it is envisioned that the invention can be applied to other conduits in the body as well including arteries, veins, bronchi, ducts, ureters, urethra, and other lumens intended for the passage of air, fluids, or solids.

While the various embodiments of the present invention have related to stents and stent delivery systems, the scope of the present invention is not so limited. Further, while choices for materials and configurations may have been described above with respect to certain embodiments, one of ordinary skill in the art will understand that the materials described and configurations are applicable across the embodiments.

What is claimed is:

1. An expandable tubular stent for implantation in a body lumen comprising:
    a structural portion extending along an axis being radially expandable thereabout and having a first expanded percentage open area, the structure portion including a plurality of struts; and
    a barrier portion affixed to the structural portion and having a second expanded percentage open area, the barrier portion including a plurality of pores extending therethrough, the barrier portion being at least partially made of metal;
    the stent having a composite expanded percentage open area within a range of 65% to 95%, wherein the composite expanded percentage open area is calculated by finding a difference between an area of the pores of the expanded barrier portion and an area of said pores occluded by the struts of the expanded structural portion, and dividing said difference by surface area of the expanded stent.

2. The stent of claim 1 wherein the stent has a composite expanded percentage open area of approximately 70%.

3. The stent of claim 1 wherein the stent has a composite expanded percentage open area of approximately 75%.

4. The stent of claim 1 wherein the stent has a composite expanded percentage open area of approximately 80%.

5. The stent of claim 1 wherein the stent has a composite expanded percentage open area of approximately 85%.

6. The stent of claim 1 wherein the stent has a composite expanded percentage open area of approximately 90%.

7. The stent of claim 1, wherein the barrier portion consists of metal.

* * * * *